(12) United States Patent
Weinacker et al.

(10) Patent No.: US 8,029,552 B2
(45) Date of Patent: Oct. 4, 2011

(54) CRANIUM FIXING DEVICE

(75) Inventors: Marcus Weinacker, Tuningen (DE);
Georg Matter, Wetzikon (CH)

(73) Assignee: Pina Medizintechnik Vertriebs AG,
Neuhausen (CH)

( * ) Notice: Subject to any disclaimer, the term of this patent is extended or adjusted under 35 U.S.C. 154(b) by 833 days.

(21) Appl. No.: 12/108,246

(22) Filed: Apr. 23, 2008

(65) Prior Publication Data

US 2008/0275511 A1 Nov. 6, 2008

(51) Int. Cl.
*A61B 17/04* (2006.01)
*A61B 17/84* (2006.01)
*A61F 2/08* (2006.01)

(52) U.S. Cl. ...................................... 606/324

(58) Field of Classification Search ............. 606/74, 606/75, 324
See application file for complete search history.

(56) References Cited

FOREIGN PATENT DOCUMENTS
WO 2005/016160 2/2005

*Primary Examiner* — Thomas C. Barrett
*Assistant Examiner* — Sameh Boles
(74) *Attorney, Agent, or Firm* — Fish & Associates, PC

(57) ABSTRACT

The cranium fixation device (1) includes a cranium clamp (2) having a first clamping element and a second clamping element (3, 4) and also a rod (5), with the rod (5) extending from the first clamping element and ending in an end portion (5d). The second clamping element (4) is displaceably arranged in the direction of extent (53) of the rod (5). A hand actuatable applicator (7) is provided and has a holding part (7a) and a thrust part (7b). The holding part (7a) and the thrust part (7b) are connected to one another via a connection part (7c). The end portion (5d) of the bar (5) is held by the holding part (7a) and the thrust part (7b) is arranged such that it can exert a force on the second clamping element (4) directed towards the first clamping element (3). The connection part (7c) extends partly spaced from the rod (5) such that a displacement of the connection part (7c) towards the rod (5) increases the distance between the holding part (7a) and the thrust part (7b) in order to thereby displace the second clamping part (4) via the thrust part (7b) acting thereon in the direction of the first clamping element (3).

12 Claims, 4 Drawing Sheets

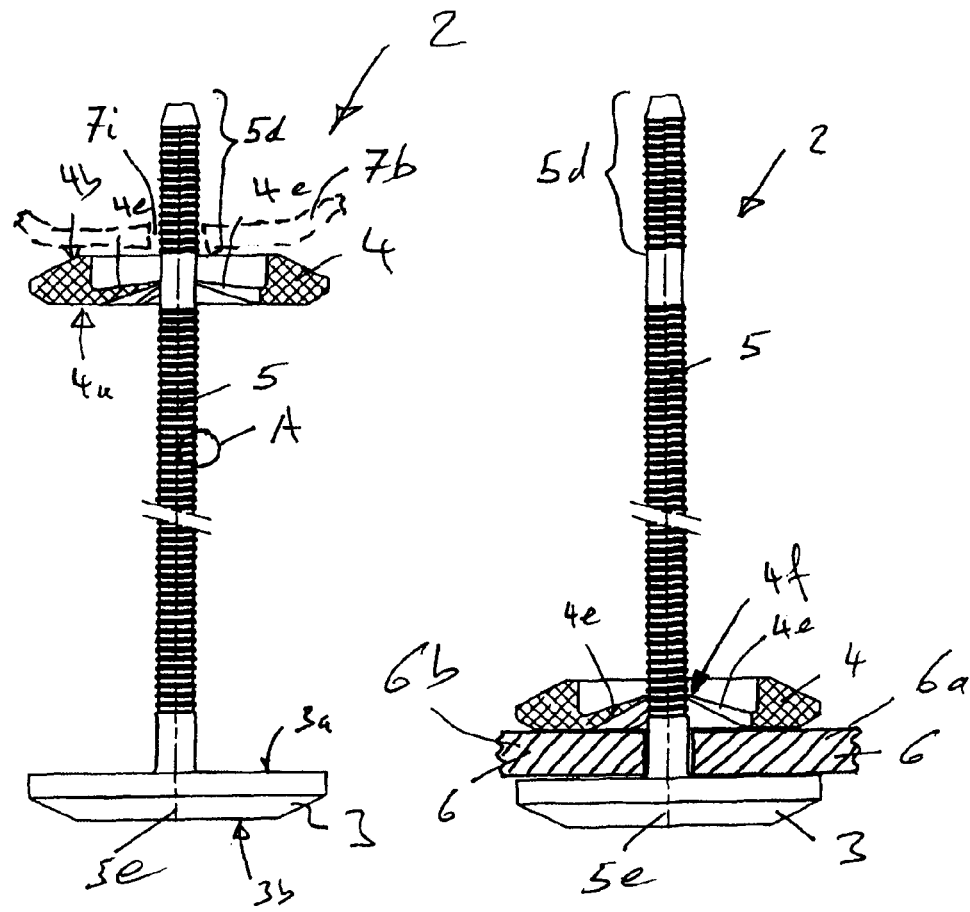

Figure 9:
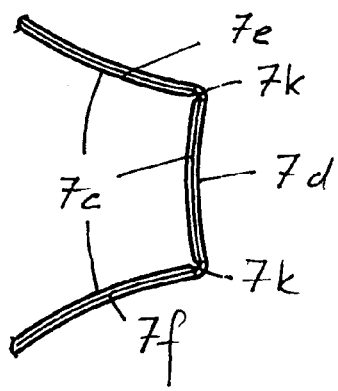

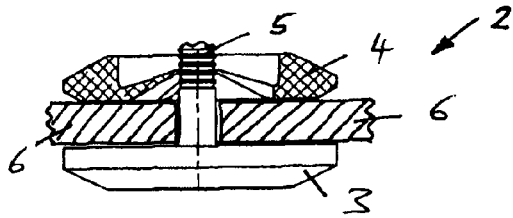
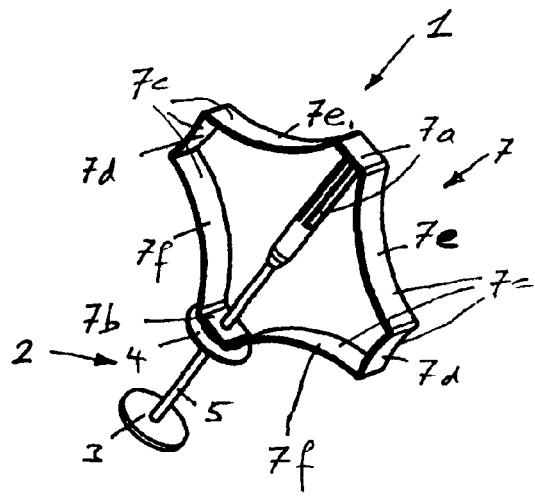
Fig. 5
Fig. 6
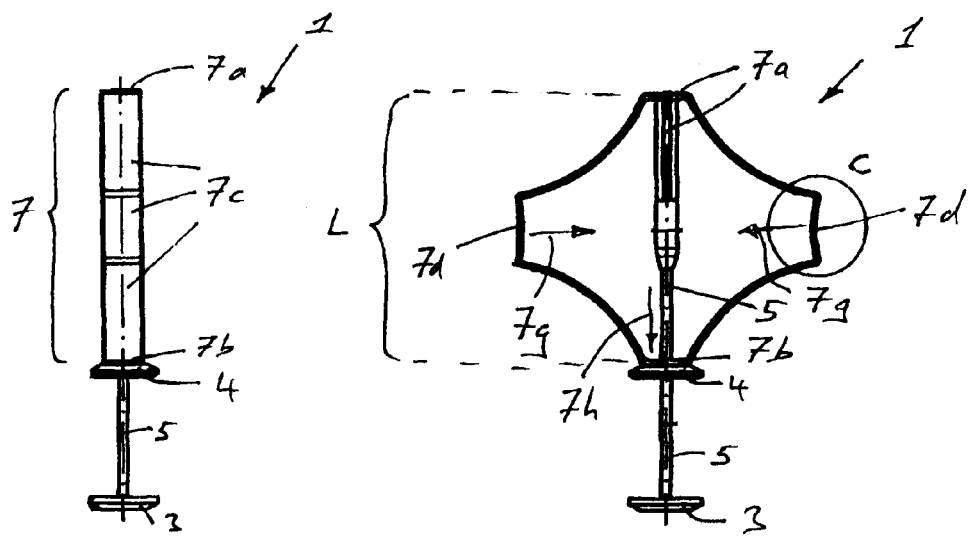
Fig. 7
Fig. 8

CRANIUM FIXING DEVICE

The invention relates to a cranium fixing device in according to the preamble of claim 1. The invention furthermore relates to a hand-actuatable applicator for the fixing of a cranium clamp in accordance with the preamble of claim 11.

PRIOR ART

The document WO 2005/016160 A1 discloses a system for the fixing of adjacent cranium bone plates. The totality of the cranium bone plates forms the cranium cap designated a cranial flap in English. The document discloses differently designed cranium clamps which can be arranged at the cranium, with different tools being disclosed in order to tighten the cranium clamp and to thereby secure it to the cranium flap.

The system disclosed has the disadvantages that it is difficult to arrange the cranium clamps on the cranial flap and it is moreover difficult to tighten the cranium clamp. For the tightening of the cranium clamps both hands are moreover required, in addition the tightening requires relatively much time.

PORTRAYAL OF THE INVENTION

The object of the invention is to form a cranium fixing device which makes it possible to arrange and to tighten the cranium clamps in a simple manner.

This object is satisfied with a cranium clamp fixing device having the features of claim 1. The subordinate claims 2 to 10 relate to further advantageously designed cranium fixing devices. The object is further satisfied with a hand-actuatable applicator having the features of claim 11.

The object is in particular satisfied with a cranium fixing device including a cranium clamp having a first clamping element and a second clamping element and also a rod, with the rod extending from the first clamping element and ending in an end portion, wherein the second clamping element is displaceably arranged in the direction of extent of the rod, wherein a hand actuatable applicator has a holding part and a thrust part, wherein the holding part and the thrust part are connected to one another via a connection part, wherein the end portion of the bar is held by the holding part, wherein the thrust part is arranged such that it can exert a force on the second clamping element directed towards the first clamping element and wherein the connection part extends partly spaced from the rod such that a displacement of the connection part towards the rod increases the distance between the holding part and the thrust part in order to thereby displace the second clamping part via the thrust part acting thereon in the direction of the first clamping element.

The cranium clamp fixing device in accordance with the invention has a hand-actuatable applicator to which the cranium clamp is connected, with the applicator having an actuating portion through the actuation of which the cranium clamp is tightened. The cranium clamp has a rod on which a clamping element is mounted for displacement along the rod. The applicator is designed such that the actuation of the actuation portion takes place transversely to the direction of extent of the rod, preferably essentially in a direction perpendicular to the direction of extent of the rod. In a preferred embodiment the cranium fixing device is held during the introduction of the cranium clamp into the cranium also at the actuating portion. This has the advantage that the cranium fixing device can be both positioned with a single hand in the cranium and thereafter the cranium clamp can be tightened and fixed by pressing on the actuating portion. Since the actuating portion is actuated transverse to the direction of extent of the rod the advantage results that the cranium clamp can be very comfortable and precisely positioned and fixed in that the cranium clamp is positioned in a first handling step and is fixed in a second handling step with a force extending transverse to the rod being exerted on the actuating portion during the fixing, which has the consequence that the cranium clamp is also kept relatively precisely in its position during the fixing so that the positioning and fixing of the cranium clamp can be carried out using a single hand. The cranium fixing device in accordance with the invention thus has the advantage that it can be fixed to the cranium flap in a reliable and quick manner which is very convenient for a surgeon. After the tightening and fixing of the cranium clamp it is only necessary to cut through the rod so that the cranium clamp is finally arranged and the next cranium clamp can be placed.

In a preferred embodiment the cranium fixing device is designed as a disposable part in that this in each case includes a hand-actuatable applicator and a cranium clamp connected thereto, with the hand-actuatable applicator being disposed off after the positioning and fixing of the cranium clamp. This design has the advantage that a surgeon can fasten a plurality of cranium clamps in a short time one after the other to the cranial flap.

In a further design the hand-actuatable applicator can also be multiply used, with the applicator having a fastening portion to which cranium clamps can be respectively fastened, in order to introduce each cranium clamp into the cranial flap and to secure it to the cranial flap. An advantage of this design can be seen in the fact that a set can be made available to the surgeon comprising an applicator and a plurality of cranium clamps and if required also differently designed cranium clamps. A further advantage of this design is to be seen in the fact that cranium clamps of other manufacturers can also be introduced into the cranium flap and secured to the cranial flap using the hand-actuatable applicator.

In the following a plurality of embodiments will be explained in detail.

SHORT DESCRIPTION OF THE DRAWINGS

Figure 10:
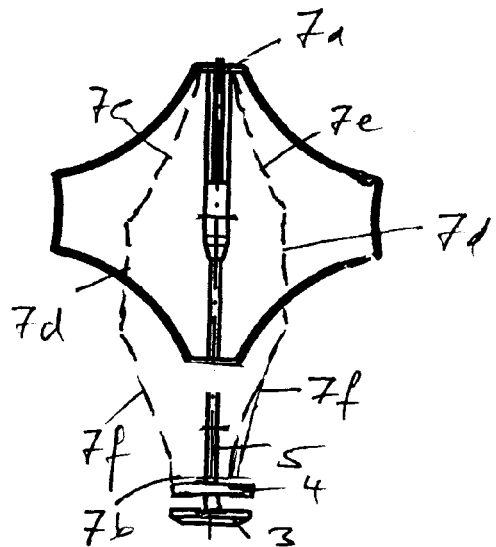
Figure 11:
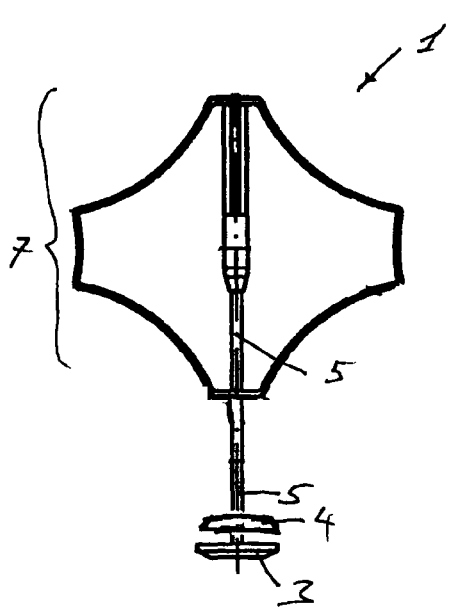
Figure 12:
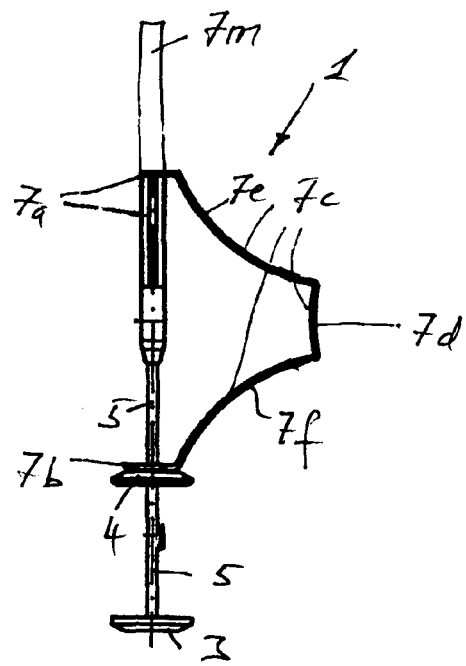
Figure 13:
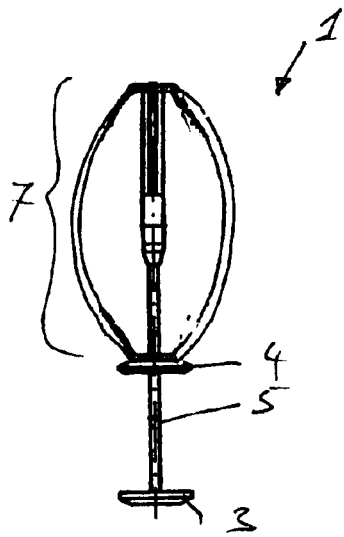
Figure 14:
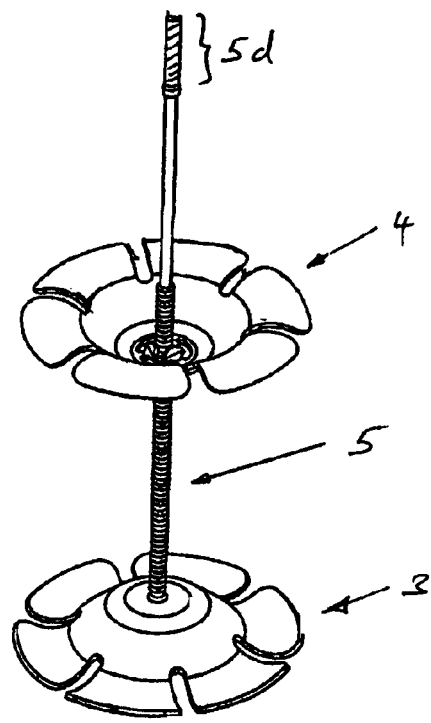
Figure 15:
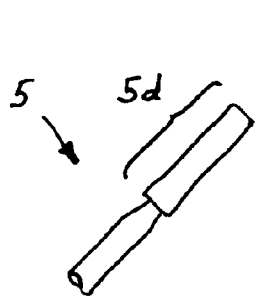
Figure 16:
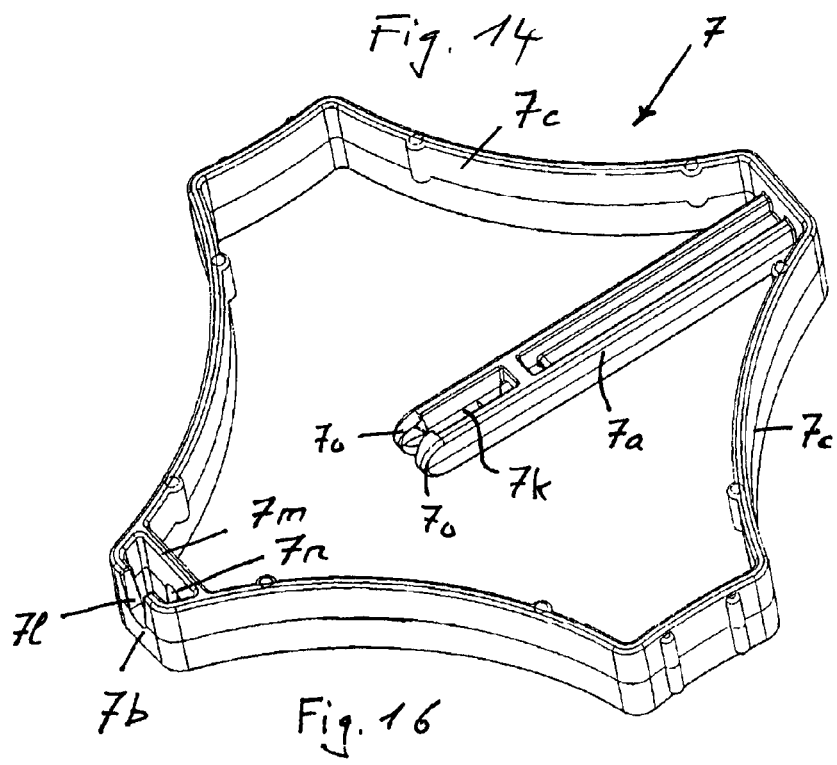

The drawings used to explain the embodiments show:

FIG. 1 a side view of a cranium clamp in the open state;

FIG. 2 a side view of a cranium clamp in the closed state;

FIG. 3 a plan view of a second clamping element of the cranium clamp;

FIG. 4 a detailed view of a rod of the cranium clamp;

FIG. 5 a side view of a cranium clamp secured to the cranium;

FIG. 6 a perspective view of a cranium clamp fixing device including a hand-actuatable applicator and also a cranium clamp;

FIG. 7 a view of the narrow side of the device shown in FIG. 6;

FIG. 8 a side view of the device shown in FIG. 6;

FIG. 9 a detailed view of a connection part of the device shown in FIG. 6;

FIG. 10 a state of the device shown in FIG. 6 during the actuation;

FIG. 11 a state of the device shown in FIG. 6 after the actuation;

FIG. 12 a side view of a further embodiment of an applicator;

FIG. 13 a side view of a further embodiment of an applicator;

FIG. 14 a perspective view of a further cranium clamp which is suitable for use with the applicator;

FIG. 15 a side view of an end portion of a rod;

FIG. 16 a perspective view of a further embodiment of an applicator.

In the drawings the same parts are basically provided with the same reference numerals.

WAYS OF CARRYING OUT THE INVENTION

As is shown in an embodiment in FIGS. 1 to 5, the cranium clamp 2 includes a first clamping element 3, a rod 5 and also a second clamping element 4 which is mounted on the rod 5 and displaceable in the direction of extent of the rod 5. The first clamping element 3 has a disc-shape with a planar inner surface 3a and a convex outer surface 3b. The rod 5 which ends in an end portion 5d extends starting from the clamping element 3. The rod 5 has a longitudinal axis 5e. In the illustrated embodiment the clamping element 3 and the rod 5 are designed as one piece. The rod 5 could however also be secured to the clamping element 3, for example by a thread. In the illustrated embodiment the rod 5 has a plurality of latching parts 5a arranged spaced apart in the direction of extent of the rod 5, each latching part 5a having a sliding point or surface 5b of inclined extent and a latching point 5c designed as a corner. The design of the latching part 5a is thus matched with respect of the second clamping element 4 so that a displacement of the second clamping element 4 is possible, as shown in the FIGS. 1 and 2, in the direction towards the first clamping element 3 whereas a displacement in the opposite direction is prevented. In order to bring this about the second clamping element 4 has an opening 4c and slots 4d extending radially to the opening 4c so that resilient tongues 4e are formed the edge of which directed towards the opening 4c engage at the latching part 4a.

FIG. 3 shows a plan view of the second clamping element 4. The FIGS. 1 and 2 show a section of the second clamping element 4 along the section line B-B shown in FIG. 3. The second clamping element 4 includes moreover an inner surface 4a and an outer surface 4b. As shown in broken lines in FIG. 1 a thrust part 7b engages at the outer surface 4b in order to exert a force on the second clamping element 4 which acts downwardly towards the first clamping element 3 in order to thereby displace the second clamping element 4 into the position shown in FIG. 2. The thrust part 7b preferably has a bore 7i which surrounds the rod 5 so that the thrust part 7b is guided by the rod in the direction of extent 53 of the rod 5.

The cranium clamp 2 shown in FIG. 1 is introduced in a first method step of the fixing of neighbouring cranium plates in such a way that the first clamping element 3 comes to lie under the cranial flap. After the positioning of the cranium clamp 2 this is tightened or brought into a clamping position in that, as shown in FIG. 2, the second clamping element 4 is displaced such that it lies on the bone plates 6, in the illustrated example a bone cover 6a and a cranium 6b. After this method step the bar 5 is cut through so that the cranium clamp 2 contacts the cranium as shown in a section and fixes adjacent cranium bone plates in their position.

The cranium clamp 2 can be manufactured from any suitable bio-compatible material such as stainless steel, titanium, an alloy based on titanium, a plastic or a resorbable material. When the cranium clamp 2 is manufactured from a metallic material the first and the second clamping elements 3, 4 and also the rod 5 are preferably manufactured of the same material. Particularly well-suited is a material of PEEK or PEKK and in particular also a material OXPEKK®. These materials have the advantage that they do not bring about any artefacts in clinical investigations such as X-ray, CT or MRT.

FIG. 6 shows in a perspective view a cranium fixing device 1 comprising a cranium clamp 2 which is connected at the connection portion 5d to a hand-actuatable applicator 7. The hand-actuatable applicator 7 includes a holding part 7a and a thrust part 7b which are connected to one another via two connection parts 7c. The two connection parts 7c are arranged so that they extend symmetrically to one another with respect to the rod 5, i.e. with respect to the axis of extent 5e of the rod 5. The thrust part 7b has, as shown in FIG. 1 in detail, a bore 7i so that the thrust part 7b is guided at the bar 5. The thrust part 7b is firmly connected to the two connection parts 7c. The connection part 7c could however also be designed such that it has a contact part arranged towards the thrust part 7b which only contacts the thrust part 7b but is not firmly connected to it.

The connection part 7c consists, following one another, of a first connection section 7e, an actuation section 7d and a second connection section 7f. The actuation section 7d preferably extends substantially parallel to the rod 5. At least one of the first and second connections 7e, 7f advantageously extend in curved manner and particularly advantageously as shown in FIG. 6 in a concave manner with respect to the rod 5. FIG. 7 shows the narrow side of the device 1 shown in FIG. 6. FIG. 8 shows a side view of the device 1 shown in FIG. 6. The hand-actuatable applicator 7 is designed such that the displacement of the two actuation sections 7d in the direction of movement 7g, that is to say towards the rod 5, has the consequence that the thrust part 7b is moved in the direction towards the first clamping element 3 which has the consequence that the second clamping element 4 is displaced by the thrust part 7b in the direction towards the first clamping element 3. The thumb preferably contacts the actuation section 7d whereas the index finger contacts the second actuation section. This enables, on the one hand, the introduction of the first clamping element 3 into the cranial flap in the position shown in FIG. 1. Thereafter the two fingers are pressed towards one another so that the actuation sections 7d move towards one another whereby the second clamping element 4 can be displaced as shown in FIG. 2 until the second clamping element, for example contacts the cranial flap 6. FIG. 10 shows in a side view the cranium fixing device 1 in this position. FIG. 11 shows in a side view the cranium fixing device 1 after the force acting on the actuating section 7 has been reduced again so that the thrust part 7b again adopts the starting position whereas the second clamping element 4 remains in the position illustrated in FIG. 2.

During the introduction of the first clamping element 3 into the cranial flap it is of advantage when the distance between the first and the second clamping elements 3, 4 is sufficiently large in order to enable the largest possible freedom of movement to the surgeon during the introduction. In order that the hand-actuatable applicator 7 with the thrust part 7b having a relatively large part of displacement it is of advantage when the spacing between the actuating section 7d and the rod 5 amounts to at least a quarter of the length L of the connection part 7c extending in the direction of extent of the rod 5. This distance preferably amounts, as shown in FIG. 8, to at least the half.

The cranium fixing device 1 is preferably designed as a disposable part and is preferably manufactured from a plastic. The cranial clamp 2 can also be releasably connected to the applicator 7, for example in that the connection section 5d is designed as a thread which is connected to a bore of the holding part 7a. The applicator 7 can for example also be designed as a multiply usable device which is equipped with cranium clamps 2.

FIG. 9 shows the section shown in FIG. 8 at C in detail. The connection part 7c which has a first connection section 7e, an actuation section 7d and also a connection section 7f can be seen, with the previously named sections 7e, 7d, 7f being connected to one another via elastic hinge points 7k. The connection part 7c is preferably manufactured from a plastic.

FIG. 12 shows in a side view a further embodiment of a cranium fixing device 1 which, in distinction to the embodiment shown in FIG. 8, only has a single connection part 7c. The applicator 7 is for example actuated in such a way that the thumb contacts the actuation section 7d whereas the index finger contacts the holding part 7a or the rod 5. In a further embodiment the applicator 7 can additionally have a holding handle 7m as shown which can serve for the improved guidance of the applicator 7.

FIG. 13 shows a further embodiment of an applicator 7 which has two connection parts 7c which both extend in curved shape.

FIG. 14 shows a further embodiment of a cranium clamp 2. The hand-actuatable applicator 7 and also the cranium clamp 2 are preferably designed so that they are mutually matched in such a way that the cranium clamps 2 can for example be fixedly connected to the applicator 7 via the connection section 5d. Thus it is possible for the applicator 7 to be used with a plurality of differently designed cranium clamps 2 in order to introduce these at the cranium flap and secure them. The connection section 5d can be connected to the applicator 7 using a plurality of different methods, for example using a screw connection, a plug connection or a crimped connection.

FIG. 15 shows a side view of a further embodiment of a connection section 5d of the rod 5. The applicator 7 shown in FIG. 16 has a holding part 7a with the holding part 7a having a cut-out 7k which is designed such that it is matched to the connection section 5d shown in FIG. 15 in such a way that the rod 5 is fixedly connectable to the holding part 7a. In an advantageous design the connection section 5d is introduced sidewise that is to say perpendicular to the direction of extent of the rod 5 into the cut-out 7k shown in FIG. 16 so that the connection section 5d comes to lie within the cut-out 7k and is thereby held.

In a further advantageous embodiment the connection section 5d can also be moved in the direction of extent in the holding part 7a i.e. in the direction of extent of the rod 5 and can be inserted starting from the jaws 7o, between the two jaws 7o and thereafter into the cut-out 7k, with the two jaws 7o preferably being resiliently or elastically designed so that the connection section 5d is only held in the holding part 7a after the insertion into the cut-out 7k.

In an advantageous embodiment the connection section 5d can be removed by a lateral movement, that is to say a movement perpendicular to the direction of extent of the rod 5, out of the cut-out 7k again so that a new rod 5 can again be anchored in the holding part 7a in the applicator 7. Thus the applicator 7 can be used a plurality of times. In a further advantageous embodiment the thrust part 7b has a groove 7l. In a further advantageous design a further guide part 7m with the groove 7n is arranged alongside the thrust part 7b. In a particularly advantageous design the grooves 7l, 7n extend perpendicular to the direction of extent of the rod 5 and in the same direction as the cut-out 7k. On removing the rod 5 from the cut-out 7k the two grooves 7l, 7n form a guide for the rod 5 so that the extent of the two grooves 7l, 7n defines the pivotal movement or pivotal direction possible for the rod 5. In a reusable applicator 7 the rod 5 must be removed again at the applicator 7 after the placement of the cranium clamp 2. The grooves 7l, 7n permit the rod 5 to be lifted out of the cut-out 7k by defined pivotal movement and thereafter to be removed from the applicator 7.

The invention clamed is:

1. A cranium fixation device (1) including a cranium clamp (2) having a first clamping element (3) and a second clamping element (4) and a rod (5), with the rod (5) extending from the first clamping element and ending in an end portion (5d), wherein the second clamping element (4) is displaceably arranged in a direction of extent (53) of the rod (5), wherein a hand actuatable applicator (7) has a holding part (7a) and a thrust part (7b), wherein the holding part (7a) and the thrust part (7b) are coupled to one another via a connection part (7c), wherein the end portion (5d) of the rod (5) is held by the holding part (7a), wherein the thrust part (7b) is arranged such that the thrust part can exert a force on the second clamping element (4) directed towards the first clamping element (3) and wherein the connection part (7c) extends partly spaced from the rod (5) such that a displacement of the connection part (7c) towards the rod (5) increases the distance between the holding part (7a) and the thrust part (7b) in order to thereby displace the second clamping element (4) via the thrust part (7b) acting thereon in the direction of the first clamping element (3), wherein the connection part (7c) has in series following one another a first connection portion (7e), an actuation portion (7d) and a second connection portion (7f), wherein the actuation portion (7d) extends substantially parallel to the rod (5), and at least one of the first and second connection portions (7e, 7f) extends in curved manner.

2. A device in accordance with claim 1, characterized in that the applicator (7) has two connection parts (7c) which are arranged symmetrically to one another.

3. A device in accordance with claim 1, wherein the thrust part (7b) has a bore (7i) through which the rod (5) extends.

4. A device in accordance with claim 1, wherein the thrust part (7b) is fixedly coupled to the connection part (7c).

5. A device in accordance with claim 1, wherein at least one of the first and second connection portions (7e, 7f extends concavely relative to the rod (5).

6. A device in accordance with claim 1, wherein the distance between the actuating portion (7d) and the rod (5) amounts to at least a quarter of a length of the connection part (7c) extending in the direction of extent of the rod (5).

7. A device in accordance with claim 1, configured as a disposable part.

8. A device in accordance with claim 1 wherein the cranium clamp (2) is releasably connected to the applicator (7).

9. A device in accordance with claim 1 wherein the second clamping element (4) has tongues (4e), wherein the rod (5) has a plurality of latch points (5c) and wherein the tongues (4e) and the latch points (5c) are configured such as to cooperate in such a way that the second clamping element (4) is hindered against executing a movement in the direction towards the connection portion (5d).

10. A device in accordance with claim 1 wherein the holding part (7a) includes a handle.

11. A hand-actuated applicator (7) for application of a cranium clamp (2) which has a first and a second clamping element (3, 4) and further has a rod (5), wherein the rod (5) extends from the first clamping element (3) and ends in an end section (5d), wherein the second clamping element (4) is displaceably arranged in a direction of extent (5e) of the rod (5), wherein the applicator (7) has a holding part (7a) and a thrust part (7b), wherein the holding part (7a) and the thrust part (7b) are coupled together via a connection part (7c), wherein the end section (5d) of the rod (5) is configured to allow fixing of the end section in a fastening section of the holding part (7a), wherein the thrust part (7b) is arranged such that the thrust part can exert a force onto the second clamping element (4) directed towards the first clamping element (3) and wherein the connection part (7c) extends partly spaced from the holding part (7a) in such a way that a displacement of the connection part (7c) towards the holding part (7a) increases the distance between the holding part (7a) and the thrust part (7b) in order to thereby displace the second clamping element (4) via the thrust part (7b) acting on it in the direction of the first clamping element (3), wherein the connection part (7c) has in series following one another a first connection portion (7e), an actuation portion (7d) and a second connection portion (7f), wherein the actuation portion (7d) extends substantially parallel to the rod (5), and at least one of the first and second connection portions (7e, 7f) extends in curved manner.

12. A kit comprising a hand-actuatable applicator (7) in accordance with claim 11 and a plurality of cranium clamps (2) which are connectable to the holding part (7a) of the applicator (7).

\* \* \* \* \*